United States Patent
Stensrud et al.

(10) Patent No.: US 10,118,886 B2
(45) Date of Patent: *Nov. 6, 2018

(54) BIOFUELS PRODUCTION FROM BIO-DERIVED CARBOXYLIC-ACID ESTERS

(71) Applicant: Archer Daniels Midland Company, Decatur, IL (US)

(72) Inventors: Kenneth Stensrud, Decatur, IL (US); Padmesh Venkitasubramanian, Forsyth, IL (US)

(73) Assignee: Archer Daniels Midland Company, Decatur, IL (US)

( * ) Notice: Subject to any disclaimer, the term of this patent is extended or adjusted under 35 U.S.C. 154(b) by 105 days.

This patent is subject to a terminal disclaimer.

(21) Appl. No.: 15/297,610

(22) Filed: Oct. 19, 2016

(65) Prior Publication Data

US 2017/0044086 A1    Feb. 16, 2017

Related U.S. Application Data

(62) Division of application No. 14/650,475, filed as application No. PCT/US2013/073793 on Dec. 9, 2013, now abandoned.

(Continued)

(51) Int. Cl.
| | |
|---|---|
| *C07C 67/08* | (2006.01) |
| *C07C 67/297* | (2006.01) |
| *C07C 29/149* | (2006.01) |
| *C07D 307/08* | (2006.01) |
| *C10L 1/02* | (2006.01) |
| *C10L 1/04* | (2006.01) |

(Continued)

(52) U.S. Cl.
CPC ............ *C07C 67/08* (2013.01); *C07C 29/149* (2013.01); *C07C 67/297* (2013.01); *C07D 307/08* (2013.01); *C10G 3/50* (2013.01); *C10L 1/02* (2013.01); *C10L 1/023* (2013.01); *C10L 1/04* (2013.01); *C10L 1/06* (2013.01); *C07C 29/147* (2013.01); *C07D 307/33* (2013.01); *C10L 2200/0469* (2013.01); *C10L 2290/26* (2013.01); *C12P 7/40* (2013.01); *C12P 7/46* (2013.01); *C12P 7/48* (2013.01); *Y02P 20/544* (2015.11); *Y02P 30/20* (2015.11)

(58) Field of Classification Search
CPC ..... C07C 67/08; C07C 67/297; C07C 29/147; C07C 29/149; C10G 3/50; Y02P 30/20; C01L 2290/26; C12P 7/46; C12P 7/40; C12P 7/48

See application file for complete search history.

(56) References Cited

FOREIGN PATENT DOCUMENTS

CA    2657666 A1 *  9/2009    ............... C12P 7/62

* cited by examiner

*Primary Examiner* — Yate' K Cutliff
(74) *Attorney, Agent, or Firm* — William B. Miller

(57) ABSTRACT

A process for producing biofuels compounds directly from carboxylic acid esters recovered from a fermentation system is described. The process involves taking a fermentation broth that has been reduced to a dry powder containing free organic acids; reacting the carboxylic acid in the powder with an alcohol solvent under a $CO_2$-containing atmosphere in substantial absence of any other acid catalyst at a reaction temperature and pressure that corresponds to supercritical, critical or near critical conditions for at least one of the alcohol or $CO_2$ to synthesize an ester, then subjecting the ester to either hydrogenolysis or hydrogenation to form a biofuel.

16 Claims, 6 Drawing Sheets

Related U.S. Application Data

(60) Provisional application No. 61/739,790, filed on Dec. 20, 2012.

(51) Int. Cl.
*C10L 1/06* (2006.01)
*C10G 3/00* (2006.01)
*C12P 7/40* (2006.01)
*C07C 29/147* (2006.01)
*C12P 7/48* (2006.01)
*C12P 7/46* (2006.01)
*C07D 307/33* (2006.01)

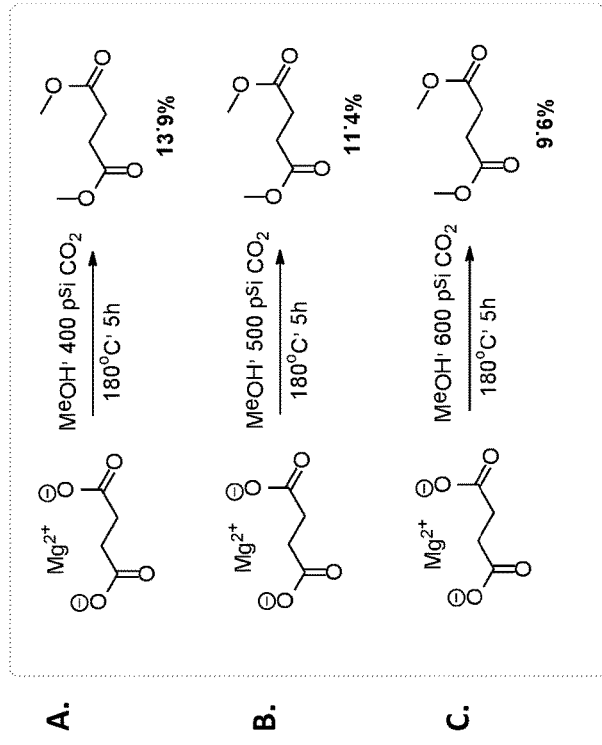
FIG. 5 Temperature Variation
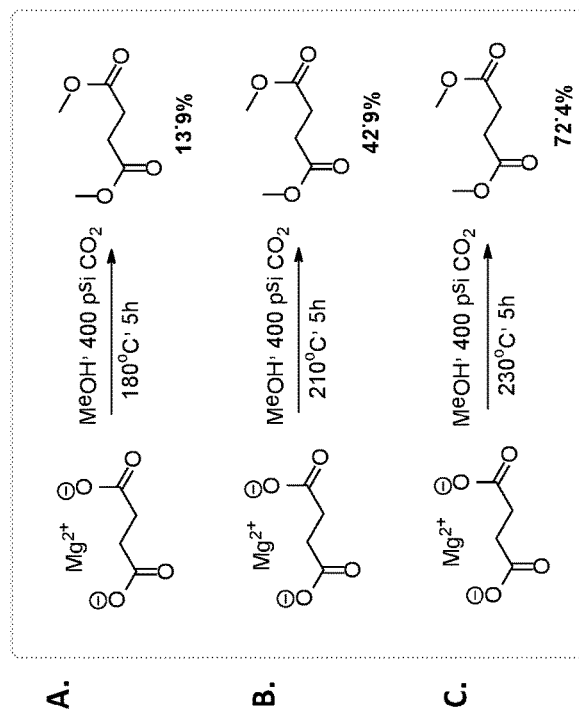
FIG. 6 Pressure Variation
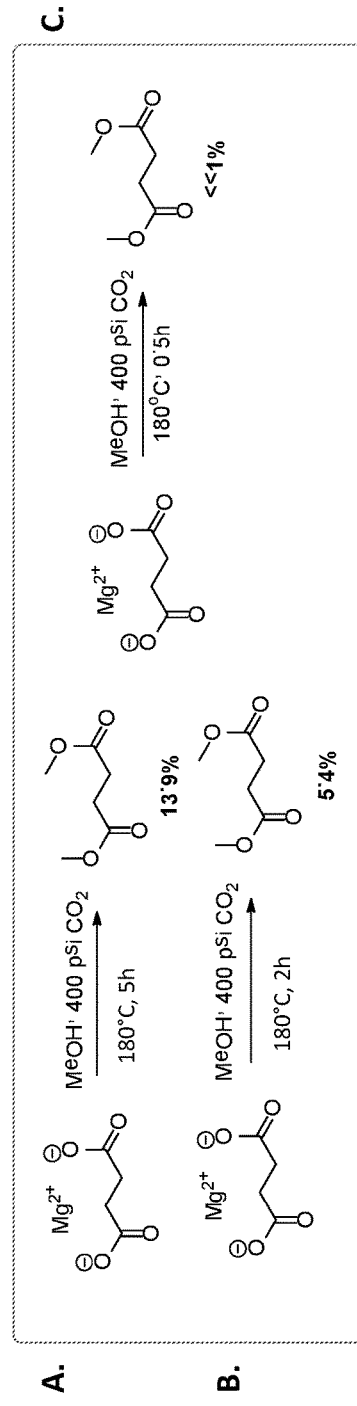
FIG. 7 Variation in Reaction Times

BIOFUELS PRODUCTION FROM BIO-DERIVED CARBOXYLIC-ACID ESTERS

PRIORITY CLAIM

The present Application claims benefit of priority from U.S. patent application Ser. No. 14/650,475, which is a national stage entry of International Application No. PCT/US2013/073793, filed Dec. 9, 2013, which itself claims benefit of priority from U.S. Provisional Patent Application No. 61/739,790, filed Dec. 20, 2012, the contents of which are incorporated herein.

FIELD OF INVENTION

The present invention relates to a process for the production of certain biofuels. In particular, the invention pertains to a method for producing biofuel products from bio-derived esters of carboxylic acids by means of either hydrogenation or hydrogenolysis.

BACKGROUND

Development of alternative fuels has gained increasing importance with increased awareness of environmental concerns and in the wake of economic pressures and fuel costs that have resulted from supply volatility of petroleum and other fossil-based resources. Policy makers have recognized this importance and have encouraged production and increased use of biofuels. As interest has grown in moving away from petrochemical or natural gas-derived hydrocarbon sources, some have concentrated on finding renewable and sustainable "green" carbon resources. Early so-called first generation biofuels are made by fermenting food products (e.g., starch-containing and sugary plants, such as corn, wheat, or sugar cane) into short-chain alcohols (e.g. ethanol, butanol) or transesterifying fatty acids liberated from plant oils by glycerolysis (e.g., rape seed, soybeans) to make fatty acid methyl esters used as biodiesel. (See e.g., Cesar B. Granda et al., "Sustainable Liquid Biofuels and Their Environmental Impact," ENVIRONMENTAL PROGRESS, Vol. 26, No. 3, pp. 233-250 (October 2007), incorporated herein by reference.)

Carboxylic acids such as used to make biodiesel can also be made by fermentation from carbohydrate sources, in addition to being derived from plant oils. Although the fermentative production of carboxylic acids, such as malic or succinic acid, has several advantages over petrochemical-based fuels, the production costs for the bio-based carboxylic acids have been too high for bio-based production to be cost-competitive with petrochemical production regimes. (See e.g., James McKinlay et al., "Prospects for a Bio-based Succinate Industry," APPL. MICROBIOL. BIOTECHNOL., (2007) 76:727-740; incorporated herein by reference.) In fermentation of starches and sugars, carboxylic acids are generated using microorganisms. Microorganisms require certain conditions for their functions. For example, with most commercially viable succinate producing microorganisms described in the literature, one needs to neutralize the fermentation broth to maintain an appropriate pH for maximum growth, conversion and productivity.

Currently, the carboxylic acids are recovered from fermentation broths as salts instead of as free acids. Typically, the pH of the fermentation broth is maintained at or near a pH of 7 by introduction of ammonium hydroxide or other base into the broth, thereby converting the carboxylic acid into the corresponding acid salt. Generation of carboxylic acid salts versus the free organic acid form brings about significant processing costs. About 60% of the total production costs are generated by downstream processing, because of the difficulties associated with the separation and purification of the acids and their salts in the fermentation broth.

Recovery of carboxylic acids as salts has a number of associated problems and requires several different steps in post-fermentation, downstream processing to isolate free acids and to prepare the carboxylic acids for chemical transformation and to convert the raw acids to useful compounds. When salts are generated in conventional fermentation processes, an equivalent of base is required for every equivalent of acid to neutralize. The amount of reagent used can increase costs. Further, one needs to remove the counter ions of the salts so as to yield free acids, and one needs to remove and dispose of any resulting waste and by-products. For instance, calcium salts of $C_4$ diacids have a very low solubility in aqueous broth solutions (typically less than 3 g/liter at room temperature), and are not suitable for many applications for which a free acid species is needed, such as chemical conversion to derivative products like butanediol and biofuels. Therefore, the calcium salt is typically dissolved in sulfuric acid, forming insoluble calcium sulfate, which can readily be separated from the free diacid. Calcium sulfate is a product having few commercial applications, and accordingly is typically discarded as a solid waste in landfills or other solid waste disposal sites. All of these individual operational units contribute to the overall costs of the process.

To reduce waste and costs associated with generating free carboxylic acids and to improve the recovery yield, a need exists for a better, more direct method of recovering a variety of carboxylic acids, such as malic or succinic acid, and which can provide a successful route to combine a biologically-derived hydrocarbon feedstock with the production of various biofuel products, such as ethane, propane, propanol or butanol, by means of hydrogenation or hydrogenolysis. Such a streamlined, green process would be a welcome innovation.

SUMMARY OF THE INVENTION

The present invention concerns a process for producing biofuels. The process involves: a) obtaining a fermentation broth containing at least one free carboxylic acid, or a mixture of carboxylic acids, or a mixture of carboxylic acids of at least one carboxylic acid and associated alkali or alkaline earth metal salts thereof; b) drying said fermentation broth containing free carboxylic acids into a powder; and c) reacting said carboxylic acids in said powder with an alcohol solvent or mixture of at least one alcohol under a $CO_2$ atmosphere in substantial absence of any other acid catalyst at a reaction temperature and pressure that corresponds to supercritical, critical or near critical conditions for the alcohol or $CO_2$ to synthesize the corresponding ester or esters; d) subjecting the esters formed to either hydrogenolysis or hydrogenation to form one or more biofuels; and e) recovering the one or more biofuels. The ester can be a mono-ester, di-ester, or tri-ester. Preferably, the ester is a di-ester or tri-ester. Monoesters can convert to mono-alcohols, diesters to diols, and triesters to triols. The biofuel products can be either an alkane or alcohol.

The esterification reaction temperature is between about 150° C. and about 250° C., and the operational reaction pressure is between about 400 psi and about 3,000 psi. Depending on the desired results, the esterification reaction can be run for at least about 4 hours.

Additional features and advantages of the present methods will be disclosed in the following detailed description. It is understood that both the foregoing summary and the following detailed description and examples are merely representative of the invention, and are intended to provide an overview for understanding the invention as claimed.

BRIEF DESCRIPTION OF FIGURES

FIG. 5 shows a series of reaction diagrams that summarize variations in temperature for $CO_2$-assisted esterification of free succinic acid derived from fermentation broth.

FIG. 6 shows a series of reaction diagrams that summarize variations in initial operational pressure for $CO_2$-assisted esterification of free carboxylic acid according to the invention.

FIG. 7 shows a series of reaction diagrams that summarize variations in temperature, and reaction times for $CO_2$ assisted esterification of free carboxylic acid according to the invention.

DETAILED DESCRIPTION OF THE INVENTION

Section I.—Description

A

Figure 1:
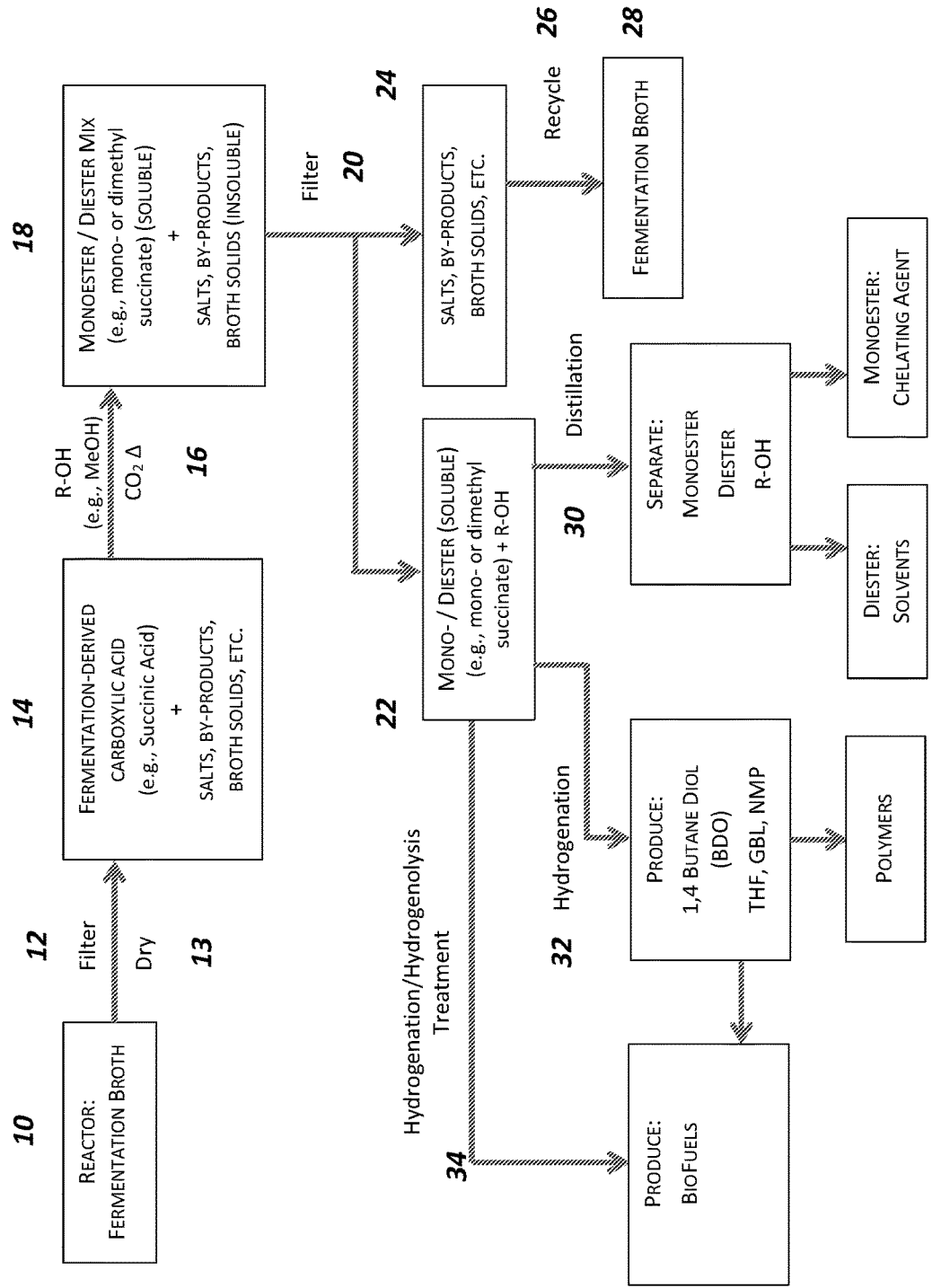
FIG. 1 is a schematic diagram illustrating an iteration of the present process for esterifying an organic carboxylic acid derived from fermentation broth, and further downstream processes that can isolate the resulting esters and/or generate other compounds from such esters.

The present disclosure describes, in part, a process for making various biofuel products by means of either hydrogenation or hydrogenolysis from a biologically-derived carbon source, such as sugar or other plant-based carbohydrates. The process joins an ability to recover a carboxylic acid from a fermentation broth, with an ability to use the acid as a feedstock for biofuel generating reactions in a streamlined procedure. The present process includes a method of converting the carboxylic acid to its corresponding ester (e.g., mono-ester, di-ester, or tri-ester) in a relatively efficient and cost effective manner.

As used herein the term "biofuels" refers to a gaseous, liquid, or solid substance that is used as a fuel, which is produced from renewable biological resources such as plant, cellulosic, or agricultural biomass or derivatives thereof. In particular, a biofuel refers to a material that can be used in or as a transportation fuel in internal combustion engines, to power certain machinery, or energy generation applications. For instance, propanol and butanol can be a gasoline additive much the same as ethanol. Butane and propane in liquefied petroleum gas (LPG) and ethane in natural gas can be adapted as fuels in certain transportation systems. Other biologically-derived hydrocarbons, like octanol/octane, or alkanes heavier than $C_5$ or $C_6$ may also be biofuels.

In particular, the present process involves obtaining a fermentation broth, from which cell mass and insoluble compounds have been either removed or not, containing a mixture of free carboxylic acid of interest, optionally with associated alkali or alkaline earth metal salts (e.g., sodium, potassium, or magnesium salts); drying the raw or clarified fermentation broth containing free carboxylic acid into a powder; reacting the carboxylic acid in the powder with an alcohol under a $CO_2$-containing atmosphere in substantial absence of any other acid catalyst at a reaction temperature and pressure corresponding to supercritical, critical or near critical conditions for the alcohol and/or $CO_2$ to synthesize an ester; and subjecting the ester to either hydrogenation or hydrogenolysis to form a biofuel product. As used herein the term "free carboxylic acid" refers to a carboxylic acid compound that is at least 50% in its protonated state when in solution, at or below its pKa value. As used herein, the term "substantial absence" refers to a condition in which an acid catalyst is either largely or completely absent, or is present in de minimis or trace amount of less than catalytic efficacy. In other words, no other acid catalyst is present, or is present at a level less than 10%, 5%, 3%, or 1% weight/weight relative to the carboxylic acid in the reaction.

In another aspect, the present invention involves the discovery of a simple but effective way of producing esters from carboxylic acids that are otherwise costly and difficult to isolate. An advantage of the present invention is that one can use free carboxylic acids directly from a fermentation broth and generate corresponding esters therefrom without the need to isolate or purify the acids from the fermentation broth, as is necessary in conventional extractions from broth.

In comparison to certain fermentation processes that neutralize or convert the organic acids to their salts, the present process provides an easier way to isolate and extract organic acids from a fermentation broth. The present process eliminates a need for titration and neutralization of the fermentation broth that can precipitate metal salts, and certain purification steps to produce a stock platform chemical. The free organic acids are converted into esters, which are simpler to process and extract by distillation or other purification techniques without the use of expensive and complicated chromatographic separation columns or resins. For instance in a conventional process, one would need to use ion exchange chromatography to isolate the acids. A small amount of salts may unavoidably carry-over after the ion exchange. Hence, one may require multiple units of operation to purify the acid to an acceptable quality level. With each added operational unit the costs of the overall process increases. In contrast with the present process in synthesizing the ester of the acid, one can recover the salt as a carbonate or hydroxide, which can be used to regenerate the fermentation broth, and minimize waste. Rather, an advantage of the present process is that one may further recycle the synthesis by-products directly back into the fermentation broth. By converting the carboxylic acids to their corresponding esters, we can avoid such issues.

B

Conventionally, esters are produced when carboxylic acids are heated with alcohols in the presence of an acid catalyst. The mechanism for the formation of an ester from an acid and an alcohol are the reverse of the steps for the acid-catalyzed hydrolysis of an ester. The reaction can go in either direction depending on the conditions used. In a typical esterification process, a carboxylic acid does not react with an alcohol unless a strong acid is used as a catalyst. The catalyst is usually concentrated sulfuric acid or hydrogen chloride. Protonation makes the carbonyl group more electrophilic and enables it to react with the alcohol, which is a weak nucleophile.

In general terms, the present esterification method involves a reaction of fermentation-derived, free organic carboxylic acid with an alcohol in a carbon dioxide ($CO_2$)-containing atmosphere in substantial absence of any other acid catalyst to produce esters. The esterification reaction is performed in solution under conditions that are either at supercritical, critical or near critical temperatures and/or pressures for either the alcohol and/or $CO_2$. Under such conditions, we believe that $CO_2$ self-generates or functions in situ as an acid catalyst, and regenerates back after the esterification reaction is completed. It is believed that a reactive intermediate (monoalkylcarbonic acid) is being made in situ in large enough quantities to drive esterification and affect ester production. This intermediate, having a similar pKa (e.g., ~4-5) as the free carboxylic acid, functions as a carbonic acid, which is much weaker than the usual strong acids. The observed trend of greater ester conversion at higher temperatures adduces a relatively large energy of activation for this process.

An advantageous feature of the inventive process is that activation of the free carboxylic acid as an acyl halide (e.g., fluoride, chloride, bromide) or by using strong mineral acids is unnecessary unlike with some other techniques. Acyl halides are inconvenient to use because these species are inherently reactive, have issues with stability, waste treatment, and can be cumbersome and costly to make.

In the present process, carbon dioxide functioning as a catalyst instead of the usual strong acids removes the need to introduce a strong acid into the esterification reaction. This feature can circumvent the usual need to adjust pH values in order to remove the catalyzing acid, enabling a simpler and cleaner synthesis. One can simply proceed to filter the resultant product to remove alkali or alkaline earth metal carbonate or other salts. A cleaner product will save costs in purification and downstream processing for conversion to other chemical feedstock.

The process described herein is a more environmentally benign way of producing esters. As it is believed that the carbon dioxide can self-generate an acid catalyst in situ in the presence of the alcohol during the esterification reaction, the present method does not require the use or addition of another acid catalyst species. In other words, the reaction kinetics with $CO_2$ alone can drive the esterification in the substantial absence of any other acid catalyst. To reiterate, the present process does not require activation of free acids as, for example, an acyl chloride or by strong acids (i.e., Fischer esterification).

In general, the esterification is conducted at an operational or reaction temperature between about 150° C. to about 250° C., at a reaction pressure of between about 400 psi and 2,500 psi, for an extended period, such as 4 hours, up to about 12 hours. Typically, the temperature can be in a range between about 170° C. or 190° C. to about 230° C. or 245° C. (e.g., 175° C., 187° C., 195° C. or 215° C.), and the operational pressure is between about 900 psi or 950 psi and about 2,200 psi or 2,400 psi (e.g., 960 psi, 980 psi, 1020 psi or 1050 psi). Alternatively, the temperature can be in a range between about 180° C. to about 245° C. (e.g., about 185° C. or 200° C. or 210° C. to about 220° C. or 235° C. or 240° C.), and the operational pressure is between about 1000 psi and 2,350 psi (e.g., 1,100 psi, 1,200 psi, 1,550 psi, 1,750 psi, 1,810 psi, or 1,900 psi). Other temperatures may be within a range, for example, from about 160° C. or 185° C. to about 210° C. or 225° C., and other operational pressures may be within a range, for example, from about 1,150 psi or 1,500 psi to about 1,800 psi or 2,000 psi.

These reaction temperatures and pressures correspond to supercritical, critical or near critical conditions for the alcohol(s) or $CO_2$. Table 1 lists, for purpose of illustration, critical parameters for some common solvents (i.e., methanol, ethanol, 1-propanol, 1-butanol, water, and $CO_2$).

TABLE 1

Critical Data for Select Substances (Yaws, C. L., Chemical Properties Handbook. In McGraw-Hill: 1999; pp 1-29.)

| Substance Name | Molecular Weight | Critical Temp. (K)/° C. | Critical Pressure (bar)/psi | Critical Density (g/cm$^3$) |
|---|---|---|---|---|
| Methanol | 32.042 | 512.58/239.43 | 80.96/1174.2255 | 0.2720 |
| Ethanol | 46.069 | 516.25/243.10 | 63.84/925.9209 | 0.2760 |
| 1-Propanol | 60.095 | 537.4/264.25 | 51.02/739.9839 | 0.2754 |
| 1-Butanol | 74.122 | 563.0 ± 0.3/289.85 | 45.0 ± 4.0/652.671 | 0.3710 |
| Water | 18.015 | 647.13/373.98 | 220.55/3198.8071 | 0.3220 |
| Carbon dioxide | 44.010 | 304.19/31.04 | 73.82/1070.6685 | 0.4682 |

At conditions above the critical point (i.e., critical temperature and/or pressure), the fluid exists in a super critical phase where it exhibits properties that are in between those of a liquid and a gas. More specifically, supercritical fluids have a liquid-like density and gas-like transport properties (i.e., diffusivity and viscosity). This can be seen in Table 2, wherein the typical values of these properties are compared between the three fluid types—conventional liquids, supercritical fluids, and gases.

TABLE 2

Comparison of Typical Physical Property Values of Liquids, Supercritical Fluids, and Gases.

| Property | Liquid | SCF | Gas |
|---|---|---|---|
| Density (g/mL) | 1 | 0.3 | $10^{-3}$ |
| Diffusivity (cm2/s) | $5 \times 10^{-6}$ | $10^{-3}$ | 0.1 |
| Viscosity (Pa · s) | $10^{-3}$ | $10^{-4}$ | $10^{-5}$ |

Likewise, "near critical" refers to the conditions at which either the temperature or pressure of at least the alcohol species or $CO_2$ gas is below but within 150K (e.g., within 50-100K), or 220 psi (e.g., within 30-150 psi) of their respective critical points. It is believed that as temperatures and pressures reach near critical, critical or supercritical conditions, the solubility of the reagents are enhanced, which promotes the esterification reaction. In other words, the $CO_2$ gas, alcohol, and acid species are better able to interact under near critical, critical or supercritical conditions than under less rigorous conditions. The reaction does not require that both the alcohol species and $CO_2$ gas be at near-critical, critical or supercritical conditions; rather, the reaction is operative as long as either one of the species satisfies such a condition.

If the present esterification reactions are operated at higher temperatures and greater pressures, up to about 250° C. and 2,500 psi or 3,000 psi, respectively, for reaction times of up to about 10 or 12 hours, one can produce significant amounts of ester product at relatively high selectivity and level of purity within a shorter reaction time than before, which was about 18-20 hours. At lower operational temperatures (<190° C.), formation of monoester molecules of polycarboxylic acids is more prevalent, while reactions at temperatures ≥190° C. or 195° C., will convert preferentially the polycarboxylic acids to diesters. By selecting a temperature in a higher range from about 190° C. or 195° C. or 200° C. to about 245° C. or 250° C., one can preferentially drive the reaction to a greater rate of diester conversion. The esterification can yield a minimum of about 50%, desirably at least 65% or 70%, of a diester of the carboxylic acid. Reactions that are performed at or near supercritical operating conditions tend to produce better results. When operated at or near critical conditions of about 230° C. or about 240° C. for methanol and about 31° C./1000 psi for $CO_2$, one is able to achieve conversions rates of about 90% or better, typically about 93% or 95%. One can achieve high yields by adjusting the permutations of different combinations of temperature and reaction times (e.g., higher temperatures and shorter reaction times (e.g., less than 10 or 12 hours, between 4 and 8 hours) or vice versa), which can be an advantage over current approaches. With optimization, esterification conducted at 250° C. under either the same or greater $CO_2$ pressure, the yield would be nearly quantitative (i.e., ≥95% yield), for example, up to about 98%, 99%, or 99.9% conversion.

As the accompanying Examples will show, variation in reaction conditions suggests that one can generate more diester product with higher temperatures and/or protracted reaction times. As stated before, however, different permutations in temperature can influence the duration of the esterification reactions to produce the same amount of ester product. The reactions according to the present method are not conducive to a significant degree of side product formation; hence one can avoid cyclization of the carboxylic acids and other starting reagents. Potential dangers of decarboxylization at high temperatures (i.e., >145° C. or >150° C.) are not observed in the present method.

Using an amount of the alcohol solvent in excess of the carboxylic acid, one can produce a very clean esterification. The present synthesis process produces very clean ester products at about 70%-72% initial purity, without generation of significant amounts of side products such as low molecular weight acids—acetic or formic acid—molecular rearrangements or cyclic products, which one could normally find in standard acid catalyzed esterification at high temperatures. The esters can be refined to achieve about 90-98% purity. The purification can be accomplished, for instance, by means of crystallization, chromatography, or distillation.

Typically, the resulting ester products can be either monoesters or diesters, or form a mixture of both. One can control the reaction to drive the esterification toward either one ester form or another. For instance, one may select an operational temperature and pressure that preferentially drives the esterification reaction towards formation of diester molecules. Likewise, one can control whether esters are formed from either a single carboxylic acid species (e.g., succinic acid) or a mixture of multiple different kinds carboxylic acids (e.g., acetic, citric, lactic, malic, maleic, succinic acids) that may be present and derivable from fermentation broth. In other words, one can use a variety of different kinds of carboxylic acids in accord with the present esterification reaction to produce a variety of different esters. These esters, in turn, can be isolated, further modified in downstream chemical processes and converted, in certain embodiments, into useful compounds such as for pharmaceutical, cosmetic, food, feed, polymer materials or biofuels. For instance, succinic esters can be converted into a polymer, such as polybutylene succinate (PBS).

In the present esterification process, both the catalyst ($CO_2$) and the esterification reagent (alcohol) are present in large excess relative to the amount of free carboxylic acid. $CO_2$ should be in the gas phase during the reaction phase, regardless of its origin (e.g., gas tank or dry ice), as the reaction is conducted at high temperatures. Addition of solid $CO_2$ is strategic in the case where sealed pressure reactors are used, in that it allows for slow sublimation of gaseous $CO_2$ formation as the reaction apparatus is being assembled. This can minimize $CO_2$ loss. In a $CO_2$ (i.e., $CO_2$-containing) atmosphere, the concentration of $CO_2$ in the reaction atmosphere can be at least 10% or 15% by volume, favorably about 25% or 30%, preferably greater than 50%. For better reaction results, the concentration of $CO_2$ should be maximized. Desirable concentrations of $CO_2$ are from about 75% or 80% to about 99.9% by volume, typically between about 85% and about 98%. Nitrogen ($N_2$) gas or air is permissible in the reactor, but preferably the concentration of gases other than $CO_2$ is kept at either a minor percentage (<50%) or de minimis amount.

Any liquid alcohol with an R-group of $C_1$-$C_{20}$ can serve as the solvent reagent or first alcohol species. The R-group can be saturated, unsaturated, or aromatic. A mixture of different kinds of alcohols (e.g., $C_1$-$C_{12}$) can also be used in the reaction, but will produce a corresponding mixture of different esters depending on the particular R-group. Certain lower alcohol species with $C_1$-$C_6$ alkyl groups are preferred as the reagent in the first esterification with $CO_2$ in view of their common availability, inexpensiveness, and mechanistic simplicity in the esterification reaction. Further, alcohols such as methanol, ethanol, propanol, or butanol are preferred because of parameters such as their comparatively simple structure and that the reactions are more easily controlled with respect to the supercritical, critical or near critical temperatures and pressures of these alcohol species. Alternatively, in some embodiments, the alcohol can also be a $C_2$-$C_6$-diol. Esterification with a diol can generate monomers or low molecular weight oligomers that can be readily polymerized.

One can use a variety of different carboxylic acids, for example, selected from the group consisting of: a) monocarboxylic acids: formic acid, acetic acid, propionic acid, lactic acid, butyric acid, isobutyric acid, valeric acid, hexanoic acid, heptanoic acid, decanoic acid, lauric acid, myristic acid, and $C_{15}$-$C_{18}$ fatty acids; b) dicarboxylic acids: fumaric acid, itaconic acid, malic acid, succinic acid, maleic acid, malonic acid, glutaric acid, glucaric acid, oxalic acid, adipic acid, pimelic acid, suberic acid, azelaic acid, sebacic acid, dodecanedioic acid, glutaconic acid, ortho-phthalic acid, isophthalic acid, terephthalic acid; or c) tricarboxylic acids: citric acid, isocitric acid, aconitic acid, tricarballylic acid, and trimesic acid. The carboxylic acids can include a mix of associated alkali or alkaline earth metal (e.g., sodium, potassium, or magnesium) salts of these carboxylic acids. Desirably, the carboxylic acid is a polycarboxylic acid, such as a dicarboxylic or tricarboxylic acid.

The process can reduce the amount of waste by means of recycling of by-products back into the fermentation broth, either in a continuous or batch process. We have also found that in the present esterification process, when free carboxylic acid is reacted with an alcohol and $CO_2$ absent any other acid catalyst, the free protonated form of the carboxylic acids has greater solubility in the alcohol solvent than their corresponding salts. Performed under similar reaction conditions, the esterification reaction using the free carboxylic acid as a reagent will yield about 2-3 times greater amount of ester product than the reaction that uses the salt species as a reagent. (This result can be seen when one compares the reaction of accompanying FIG. 3B (free acid) with that of FIG. 5A (acid salt), and in Table 4, Examples 2 and 3 (acid salt), with Examples 5 and 6 (free acid), respectively.) It is believed that solubility is a factor for the difference. For instance, since the solubility of magnesium salts in methanol and ethanol are significantly better than that of calcium salts, product yield from a reaction of a calcium salt is much lower than that produced from a starting reagent of a corresponding magnesium salt.

The present invention includes a method for esterifying a polycarboxylic acid. The esterification method involves: providing and reacting a solution of one or more free carboxylic acids with an alcohol in $CO_2$ atmosphere without the presence of any other acid catalyst; and selecting an operational reaction temperature or reaction pressure corresponding to supercritical, critical or near critical conditions for the alcohol and/or $CO_2$ to yield an ester. The reaction temperature and pressure conditions preferentially drive the reaction towards the formation of at least diester molecules over monoester molecules when the carboxylic acid is a polycarboxylic acid. As with the recovery process, the operational reaction temperature is between about 150° C. and about 250° C., and the operational reaction pressure is between about 400 psi and about 2,500 psi. Depending on the desired results, the reaction can be run for up to about 12 hours.

C

The esterification process described above can be integrated into fermentation-based production of carbon chain feedstocks and to provide a more convenient method of generating esters from carboxylic acids derived from a renewable source. The present invention provides a direct route by which biologically-derived carboxylic acids can be recovered in a simple, cost-efficient process from a fermentation broth, converted into esters, and then subjected to hydrogenation or hydrogenolysis to make biofuels. The accompanying figures illustrate how the esters are integrated into further downstream processes.

FIG. 1 is a schematic representation showing a general process of extracting carboxylic acids from fermentation broth that includes a version of the present esterification reaction integrated with further processes that can utilize the resulting esters. As shown, fermentation broth 10 from a reactor is filtered (ultra) 12 to remove biomaterials such as cell mass, and yield carboxylic acids including their salts, by products and other compounds. All of these materials are then dried 13 to make an unrefined mixture 14. This dried mixture of materials is then reacted 16 in a liquid system with an alcohol (R—OH; R=alkyl $C_1$-$C_{12}$) and $CO_2$ at an elevated operational reaction temperature and pressure to yield either monoesters or diesters, or a mixture of both. Only the carboxylic acids react in solution. The resulting mixture 18 is filtered 20 to separate the esters 22 and other by-products 24. The esters are soluble while other by-product compounds are insoluble. The by-products include carbonate salts of calcium, magnesium, or sodium, which can be recovered and recycled 26 back into a fermentation broth 28 in the reactor 10. This recycling can lead to significant cost savings and improves the efficiency of the overall fermentation and extraction process. The esters can be processed subsequently either by distillation 30, hydrogenation 32, or hydrogenloysis treatment 34, respectively, to separate the different esters, produce $C_4$ platform compounds and biofuels (e.g., ethane, ethanol, butane, butanol, etc.).

Through the distillation process one can concentrate the esters by driving off the alcohol, and then filter the by-products resultant from ester synthesis. Further distillation of a mixed-acid ester product mixture according to the boiling points of the different ester species, permits one to separate the various individual esters. For instance, Table 3 provides boiling points for a sample of common esters that may be present in an ester product mixture according to the present invention.

TABLE 3

Boiling Points for Some Common Esters

| Ester Species | Boiling Point (° C.) | Ester Species | Boiling Point (° C.) |
|---|---|---|---|
| methyl-acetate | 56.9 | ethyl-acetate | 77.1 |
| methyl-formate | 32 | ethyl-formate | 54.0 |
| methyl-lactate | 145 | ethyl-lactate | 151-155 |
| dimethyl-malate | 104-108 (1 mmHg) | diethyl-malate | 281.6 |
| dimethyl-succinate | 200 | diethyl-succinate | 217-218 |
| trimethyl-citrate | 176 (16 mmHg) | triethyl-citrate | 235 (150 mmHg) |

After recovering the esters in the remaining solution, the materials are in a readily usable form and one can either distill the ester mixture to separate the different ester species and any remaining alcohol. Once the esters are recovered, one can use the monoesters as precursors for conversion into chelating agents, and the diesters as solvents.

An advantage of recovering the carboxylic acids from fermentation in the form of their corresponding esters is that downstream processing of the esters is less energy intensive than the hydrogenation of the free acids. Another advantage of the present esterification process is that, one will find the present process simpler and easier, as compared to other approaches, to refine carboxylic acids for $C_4$ chemical platforms from fermentation. It simplifies efforts to separate esters from the other insoluble materials, as well as minimizes the amount of salt that one needs to separate. In an integrated process enables one to directly esterify a combination of free acid and salts that is produced in a low-pH fermentation, in which the fermentation is operated at a pH of less than the pKa of the carboxylic acids.

Figure 2:
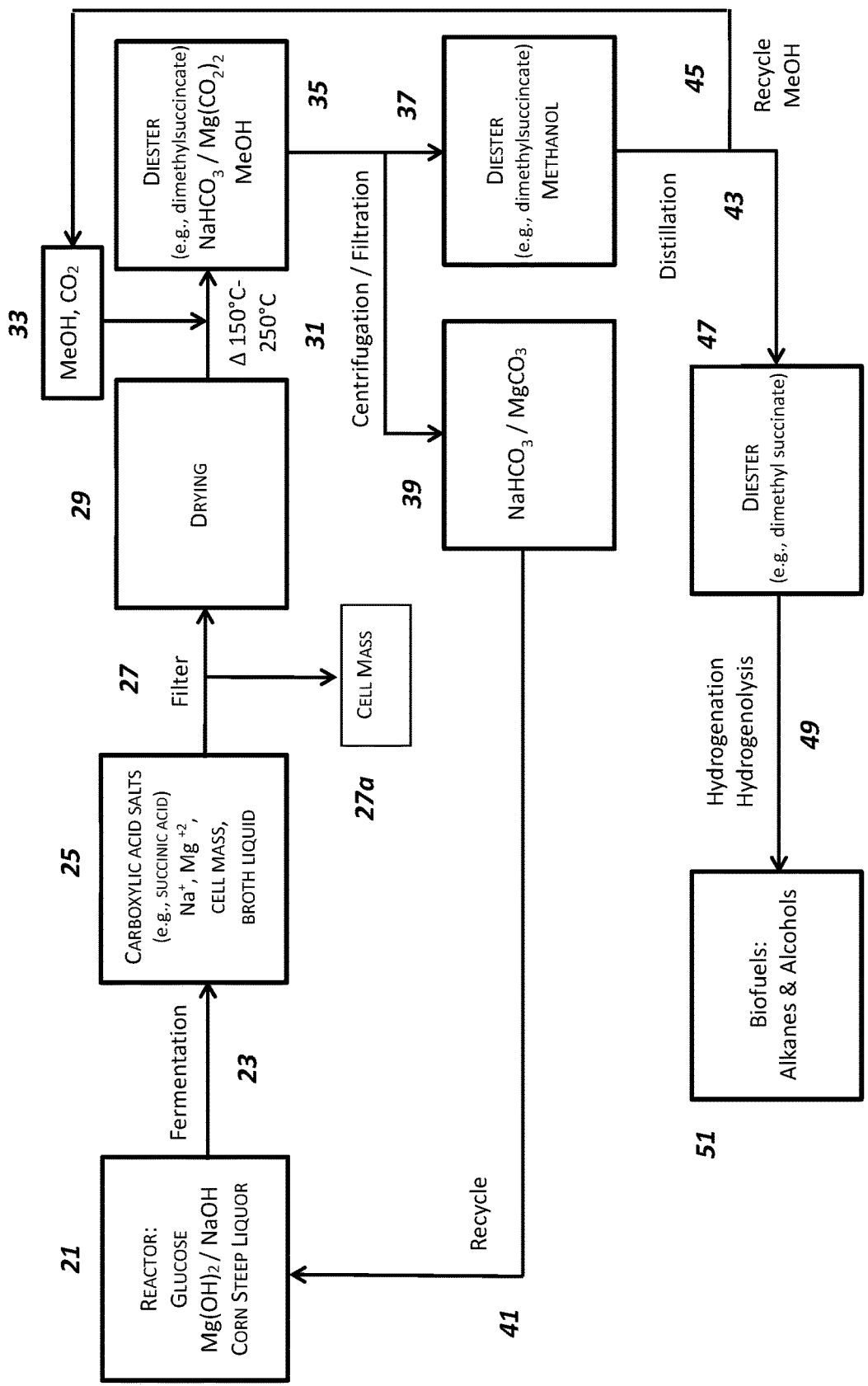
FIG. 2 is a schematic diagram showing an example of ester production using succinic acid derived from fermentation, and a downstream process in which Na and Mg salts are recycled back into the fermentation reactor, in accordance with a part of an embodiment of the present process.

FIG. 2 shows a schematic diagram of a downstream processing that incorporates an iteration of the present esterification process. In particular, FIG. 2 depicts an example of using succinic acid or any other kind of carboxylic acid derived from a fermentation broth is extracted and reacted with an alcohol in the presence of excess $CO_2$ to generate esters. According to this iteration of the process, glucose, corn steep liquor, or other sugars, and $Mg(OH)_2$/NaOH are introduced into a fermentation reactor 21 and fermented 23 to produce carboxylic acids. A fermentation broth liquid 25 containing a mixture of carboxylic acids, salts (e.g., succinic acid and its sodium or magnesium salt), and other by-products is filtered 27 to remove cell mass and other insoluble matter 27a. The fermentation is performed at a low pH value, in which one starts at a higher pH (e.g., pH ~7 or 8) and during the course of the fermentation, the pH value drops to about 2-3. One will produce a mixture of salts and free acid present, for example, in a ratio range of about 9:1 w/w to 7:3 w/w of salt to acid. The fermentation broth is retrieved from a fermentation reactor at a pH value of less than the pKa of the carboxylic acids, (e.g., pH 5). Typically, the fermentation broth is at a pH value in a range between about 1.5 and about 4.5.

The broth extract is then dried 29 to a powder. When drying the mixed acid filtrate should remove as much water as possible. The drying step can be accomplished, for instance, by means of spray drying, drum drying, or cryo-desiccation. As with esterification in general, relatively low water content is desired, otherwise the reversible reaction will tend to hydrolyze back to the dicarboxylic acid. In the present process, a maximum residual moisture content of about 5% by weight should be maintained. One would expect an increase in ester yield of up to about 98 or 99% with samples that contain less than 3% wt. of water.

The dried powder (average moisture content between about 1 wt. % and 5 wt. %, desirably ≤3 wt. %) is then reacted 31 with an alcohol 33 which serves as an alkylating agent, in excess $CO_2$ at a temperature between about 180° C. to about 250° C. for a duration of about 4 hours or more to esterify the carboxylic acids. In this example, succinic acid is reacted in methanol and $CO_2$ to generate dimethyl succinate. Along with the free carboxylic acid, any remaining free amino acids which were in the fermentation broth are also esterified.

Once the carboxylic acid esters are generated and recovered from the fermentation broth they can be further processed as feed stock in either hydrogenation or hydrogenolysis systems. Hydrogenation or hydrogenolysis can be conducted according to various different methods, systems, and their permutations, such as described in U.S. Pat. No. 7,498,450B2 (relating to homogenous hydrogenation of dicarbocilic acids and/or anhydrides), U.S. Pat. No. 6,433,193B, or 5,969,164, (relating to a process for production of tetrahydrofuran and γ-butyrolactone by hydrogenation of maleic anhydride); U.S. Pat. No. 4,584,419A (relating to process for the production of butane-1,4-diol involving the hydrogenation of a di($C_1$ to $C_3$ alkyl) ester of a $C_4$ dicarboxylic acid); UK Patent Application No. GB2207914A (relating to a process for production of a mixture of butane 1,4-diol, γ-butyrolactone, and tetrahydrofuran from maleate and fumerate); International Patent Application Nos. WO8800937A (relating to a process for the co-production of butane-1,4-diol and γ-butyrolactone by means of hydrogenation of dialkyl maleate) or WO 82/03854 (relating to a process for hydrogenolysis of a carboxylic acid ester), or an article by S. Varadarajan et al., "Catalytic Upgrading of Fermentation-Derived Organic Acids," BIOTECHNOL. PROG. 1999, 15, 845-854, the content of each of the preceding disclosures is incorporated herein in its entirety by reference.

As the example illustrates in FIG. 2, when reacted with methanol in accord with the reaction temperatures and pressure parameters defined above, succinic acid esterified to produce dimethyl succinate (as predominant product), $NaHCO_3$, $MgCO_3/Mg(HCO_3)_2$ and excess methanol 35. The dimethyl succinate and methanol 37 are separated from $NaHCO_3$ and $MgCO_3$ 39. The carbonates, unlike $CaSO_4$, can be recycled 41 back into the reactor 21, either for a continuous process or in a fresh batch process. The dimethyl succinate and methanol are further separated 43 from each other with the methanol 33 being recycled 45. Subsequently, the dimethyl succinate 47 is subjected to either hydrogenation or hydrogenolysis 49 and transformed into a variety of biofuel products 51, including alkanes and/or alcohols, for instance: ethane, ethanol, propane, propanol, butane, or butanol.

Another advantage of the present process is that it can simplify the transport and processing of crops for fermentation products. For instance, with a dried fermentation broth powder one is freed from issues associated with working with wet or liquid stock. A dried fermentation broth powder can be more economically shipped to a location different from where the fermentation broth is made or obtained. This will enable the reaction for ester synthesis to be performed at a remote location different from where the fermentation broth is obtained, and expand the geography of where the final processing facilities can be situated.

Section II.—Examples

A

Examples prepared according to the present esterification method are integrated into a process for isolating free carboxylic acid from a fermentation broth. The method involves generally the following steps: a) filtering a crude fermentation broth to remove cell mass and other biological debris from a fermentation broth; b) desiccating the fermentation broth; c) reacting the dried fermentation broth with an excess of methanol ($CH_3OH$) or ethanol ($C_2H_5OH$) and carbon dioxide ($CO_2$) at a temperature about 150° C. up to the near critical or critical temperature and under near critical or critical pressure of the alcohol and/or $CO_2$ reagents, to produce a mixture of monoesters and diesters and carbonate (NaHCO3/$MgCO_3$); d) filtering the reaction product to remove by-products; and e) purifying by distilling the esters.

The fermentation broth filtrate was dried to remove all or nearly all of the water to produce a powder of mixed organics. Using a spray dryer or drum dryer, one aerosolizes the raw solution containing mixed carboxylic acids to desiccate into a powder. The desiccated powder is suspended in an alcohol solvent. The powder reacts with the alcohol according to the conditions described herein to esterify into either monoesters or diesters.

Each of the following examples was performed according to the following general protocol, except for variations in reaction temperature, pressure, time, and/or acid species as indicated, mutatis mutandis. Ten grams of freeze-dried succinic acid fermentation broth (off-white powder) and 300 g of methanol were charged to a 1L stainless steel vessel, jacketed, and fixed to a Parr reactor. While stirring mechanically at 1100 rpm, the internal headspace of the reactor vessel was purged with $N_2$ and then pressurized initially to 400 psi with $CO_2$ and heated to 180° C. for 5 hours. The internal pressure was observed to be ~1650 psi at 180° C. After the reaction time, the reactor body was cooled in a water bath until reaching room temperature and pressure released. The heterogeneous mixture was then filtered and solids were dried overnight under vacuum. Samples of the solid material and the solution were analysis quantitatively using gas-chromatography/mass spectrometry (GC/MS). The yield of dimethyl succinate was determined to be 31.9% with more than 95% of the available magnesium succinate consumed in the reaction. The remaining balance of product included the corresponding monoesters as the greater part, and was in a range of about 60% to about 65%.

As the reactions depicted in the accompanying figures and tables show, modification and selection of certain temperature and pressure parameters causes reactions to yield preferentially more of the diester compounds. In certain examples of the present process, the esterification reactions yielded more than 50%, typically more than 70% or 80% di-alkyl succinate or malate. As stated before, the unreacted materials and the undesired products are recycled into the fermentation reactor. Subsequent separation of the mono-esters and di-esters was achieved by crystallization.

Figure 3:
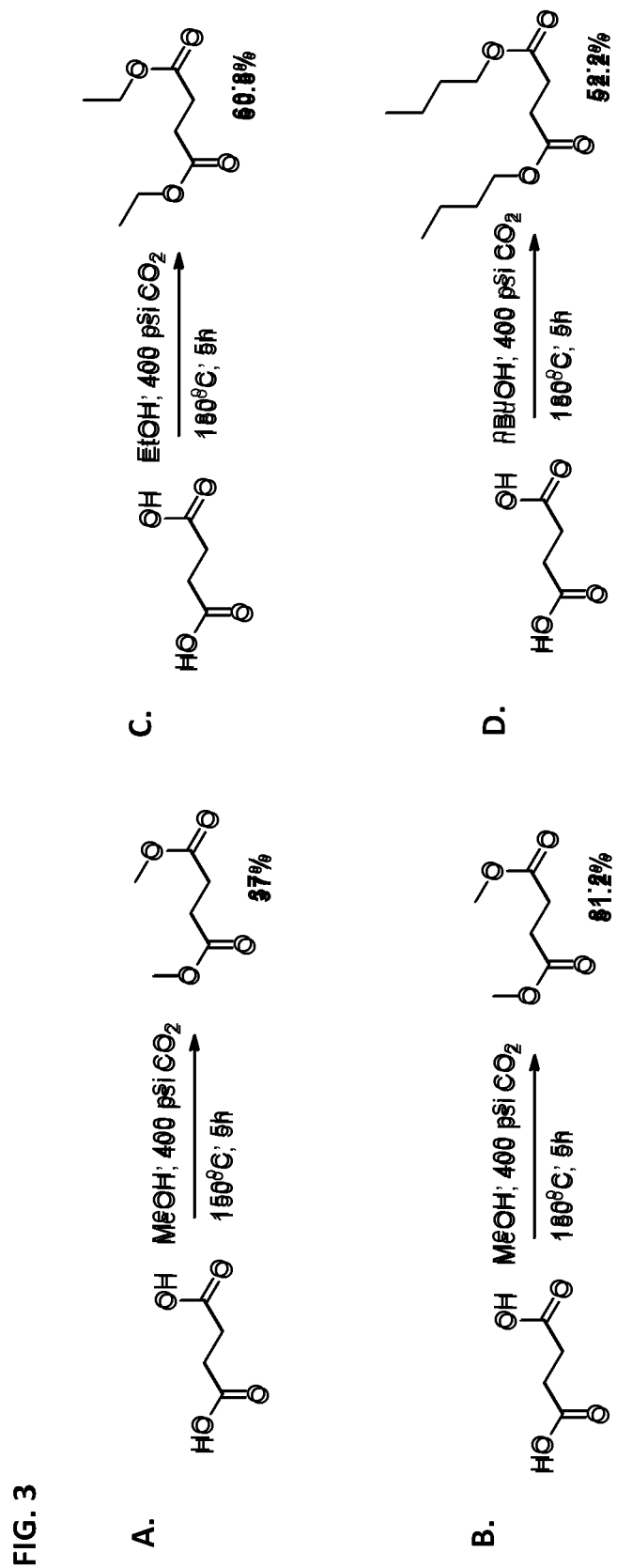
FIG. 3 is a diagram that illustrates $CO_2$-assisted esterification of free succinic acid in various alcohols that are converted to corresponding dimethyl, diethyl, or dibutyl esters, according to the present invention.

FIG. 3 shows a series of esterification reactions which summarize $CO_2$-assisted esterification of free succinic acid in various alcohols. FIG. 3A shows succinic acid reacted with methanol in 400 psi $CO_2$ gas, at 150° C. for 5 hours, which achieved a yield of about 37% dimethyl succinate. When the operational temperature was increased to 180° C. in the reaction of FIG. 3B and all other parameters kept the same as in FIG. 3A, the amount of dimethyl succinate yield increases more than two-fold to about 81.2%.

FIG. 3C represents free succinic acid reaction at 180° C. under present operational conditions in ethanol, which generates diethyl succinate in good yield of about 60.8%. In FIG. 3D, free succinic acid was reacted at 180° C. under operational conditions in n-butanol, which generates dibutyl succinate at about 52.2% yield. These examples demonstrate the versatility of the present esterification reaction in view of different kinds of alcohols.

Figure 4:
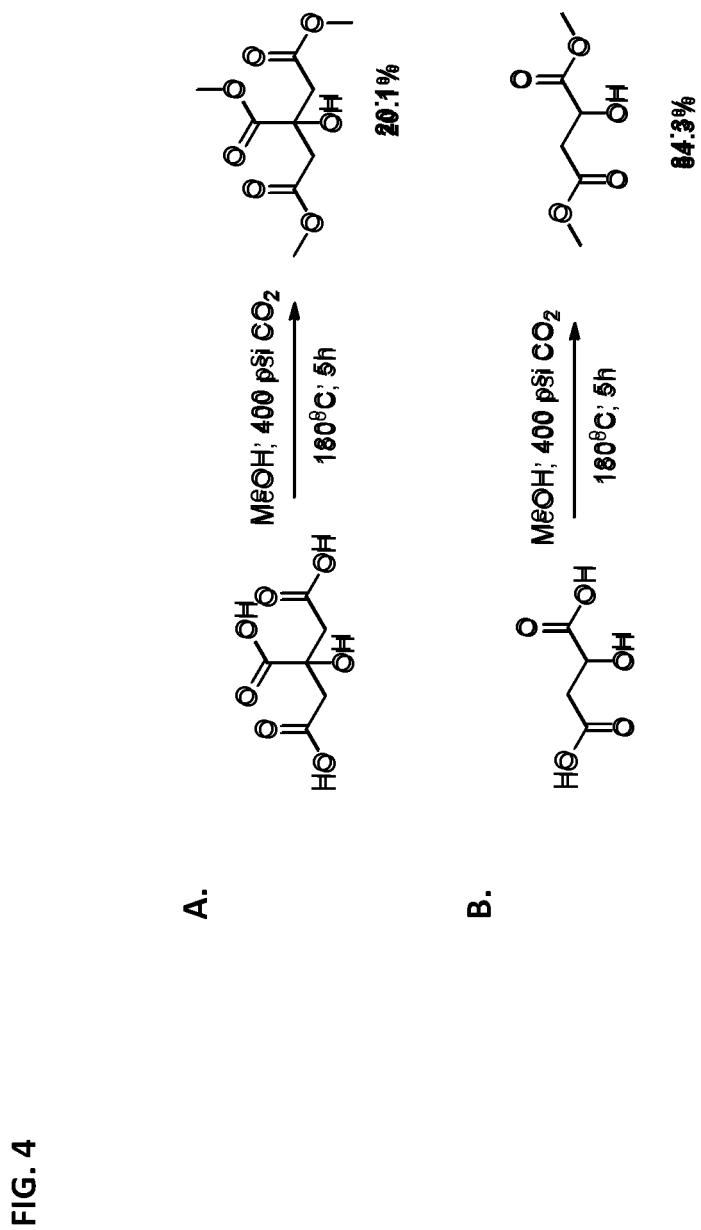
FIG. 4 is a diagram that illustrates $CO_2$-assisted esterification of other polycarboxylic acids.

FIG. 4 shows examples of $CO_2$-assisted esterification of other kinds of carboxylic polyacids. In FIGS. 4A and 4B, succinic acid was substituted respectively with citric acid, a tricarboxylic acid, and malic acid. The yield of triethylcitrate was reasonable at about 20.1%, demonstrating that the $CO_2$-assisted protocol can be applied to tricarboxylic acids. The yield of the dimethyl analogue of malic acid was good at about 84.3%. Hence, the new method of esterification is feasible for general use with other acids.

Table 4 summarizes results of several reactions that were performed according to the esterification method of the present disclosure as depicted in FIGS. 5, 6, and 7. Each set of examples is arranged in terms of a variation of an operational condition under which the reaction was performed: A) temperature, B) pressure, and C) reaction time. In each of the examples, succinic acid from a fermentation broth is used as the substrate. The filtered clarified broth containing free acid and salts are dried and later reacted with methanol and $CO_2$ in solution. (As the reactions are heated, the actual operational temperatures and pressures within the reactor vessel will exceed the initial temperatures and pressures provided herein.)

In the three examples of Set A, we carried out the reaction for 5 hours at an initial $CO_2$ pressure of 400 psi, under different temperatures: Ex. A-1 at 180° C., Ex. A-2 at 210° C., and Ex. A-3 at 230° C. The percent conversion of acid to its corresponding diester increased with higher operational temperature. FIG. 6 shows the effect of varying temperature in a series of esterification reactions of succinic acid and its salt. In FIG. 5A, the esterification of succinic acid is performed at a temperature of about 180° C., over a period of 5 hours. The reaction produced about 13.9% yield of dimethyl succinate. FIG. 5B shows the same reaction as in FIG. 5A, when the reaction time held constant, but with the temperature raised to about 210° C., which yields about 42.9%. FIG. 5C shows a reaction at 230° C. and yields about 72.4%. This suggests that as the temperature increases, the reaction kinetics drives toward a more complete reaction of the acid and alkylating agent, and a greater yield of the dialkyl-ester. Reactions performed at or near critical temperature and/or pressure conditions can produce at least 95%, likely ≥97% or 98%, conversion.

In Set B and FIG. 6, we performed the esterification reaction for 5 hours at an initial temperature of 180° C., and varied the initial $CO_2$ gas pressures: Ex. B-1 at 400 psi, Ex. B-2 at 500 psi, and Ex. B-3 at 600 psi. The percent conversion of acid to its corresponding diester was moderate, and the amount yield did not show significant difference statistically. The initial $CO_2$ gas pressure in the reactor did not exert much effect in conversion of the acid to its diester, but the operational pressures in the reactor during the reaction suggest an effect on yields.

In Set C and FIG. 7, we performed the esterification reaction at a constant pressure and temperature but varied the duration of the reaction. Ex. C-1 at 5 hours, Ex. C-2 at 2 hours, and Ex. C-3 at 0.5 hours. The examples shown in FIG. 8 suggest that a greater amount of diester was converted from the acid with increased reaction time.

Figure 8:
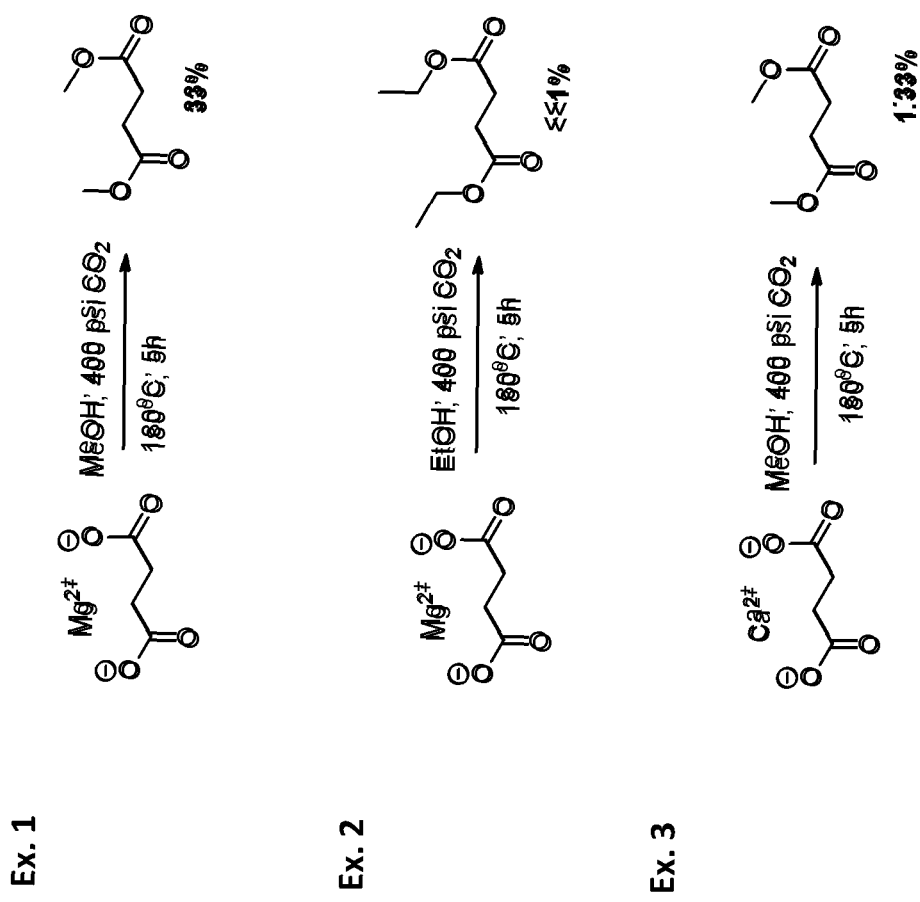
FIG. 8 shows a series of reaction diagrams that summarize the results of reaction succinic acids and their $Mg^{2+}$ and $Ca^{2+}$ salts.

FIG. 8 shows a first set of $CO_2$-assisted esterification reactions using a concentration of succinate salts of about 4% w/w, which are presented as Examples 1-3 in Table 5. In Examples 1 and 2, succinic acid and its magnesium ($Mg^{2+}$) salt was reacted in methanol and ethanol at 210° C. and 180° C., respectively, for a reaction time of 5 hours. The reactions produced about 33% dimethyl succinate and about 1% diethyl succinate, respectively. Methanol exhibits a greater capacity to dissolve the succinate salt than ethanol. Magnesium succinate exhibits a reasonable level of solubility in methanol, while it exhibits limited solubility in ethanol, even at high temperatures. Hence, the yield of diethylsuccinate was negligible. Example 3 shows a reaction using calcium ($Ca^{2+}$) succinate, at 180° C., over 5 hours. The reaction yields only about 1.33% of the corresponding dimethylsuccinate. Relatively low conversion rates in Examples 2 and 3, also highlights the solubility difference between corresponding alkali earth salts. The calcium succinate salt is insoluble in methanol, even at high temperatures. The methanol to salt molar ratio used in the $CO_2$ experiments was approximately 110:1 for methanol to magnesium succinate. Likewise, the ratio was about 100:1 for methanol to the other carboxylic acids.

TABLE 4

Variations in Reaction Conditions

| Example | Substrate | Alcohol | Reaction Time (h) | Temperature (° C.) | Initial $CO_2$ pressure (psi) | % Conversion to Diester | |
|---|---|---|---|---|---|---|---|
| A | | | | | | | |
| 1 | Succinic acid fermentation broth, $Mg^{2+}$ salt | Methanol | 5 | 180 | 400 | 13.9 | |
| 2 | Succinic acid fermentation broth, $Mg^{2+}$ salt | Methanol | 5 | 210 | 400 | 49.2 | Temperature Variation |
| 3 | Succinic acid fermentation broth, $Mg^{2+}$ salt | Methanol | 5 | 230 | 400 | 72.4 | |
| B | | | | | | | |
| 1 | Succinic acid fermentation broth, $Mg^{2+}$ salt | Methanol | 5 | 180 | 400 | 13.9 | |
| 2 | Succinic acid fermentation broth, $Mg^{2+}$ salt | Methanol | 5 | 180 | 500 | 11.4 | Pressure Variation |
| 3 | Succinic acid fermentation broth, $Mg^{2+}$ salt | Methanol | 5 | 180 | 600 | 9.6 | |
| C | | | | | | | |
| 1 | Succinic acid fermentation broth, $Mg^{2+}$ salt | Methanol | 5 | 180 | 400 | 13.9 | |
| 2 | Succinic acid fermentation broth, $Mg^{2+}$ salt | Methanol | 2 | 180 | 400 | 5.4 | Reaction Time Variation |
| 3 | Succinic acid fermentation broth, $Mg^{2+}$ salt | Methanol | 0.5 | 180 | 400 | ND | |

TABLE 5

| Example | Substrate | Alcohol | Reaction Time (h) | Temperature (° C.) | Initial $CO_2$ pressure (psi) | % Conversion to Diester | Note |
|---|---|---|---|---|---|---|---|
| 1 | Succinic acid, $Mg^{2+}$ salt | Methanol | 5 | 210 | 400 | 33.4 | Control |
| 2 | Succinic acid, $Mg^{2+}$ salt | Ethanol | 5 | 180 | 400 | 1.0 | Limited solubility |
| 3 | Succinic acid, $Ca^{2+}$ salt | Methanol | 5 | 180 | 400 | 1.3 | Limited solubility |
| 4 | Succinic acid | Methanol | 5 | 150 | 400 | 37.0 | |
| 5 | Succinic acid | Methanol | 5 | 180 | 400 | 81.2 | |
| 6 | Succinic acid | Ethanol | 5 | 180 | 400 | 60.8 | |
| 7 | Succinic acid | 1-Butanol | 5 | 180 | 400 | 52.2 | |
| 8 | Citric acid | Methanol | 5 | 180 | 400 | 20.1 | |
| 9 | Malic acid | Methanol | 5 | 180 | 400 | 86.3 | |

Table 5 lists results from other examples of esterification reactions according to the present method. Examples 1, 2 and 3 demonstrate the importance of substrate solubility of succinic acid as compared to the salts of succinate. Examples 4-7 is a second set of reactions in which free succinic acid was reacted in methanol, ethanol, and 1-butanol in similar fashion. Examples 8 and 9 show that reactions with other carboxylic acids, such as citric acid and malic acid can achieve relatively good yields of about 20% and 86%, respectively.

Free succinic acid reacts readily with the alcohols, since it is completely soluble in methanol, ethanol, butanol, and other alcohols up to and including octanol (C-8 alcohol). In Examples 6 and 7, succinic acid reacted in ethanol and 1-butanol, yields 60.8% and 52.2% conversion, respectively.

The solubility of carboxylic salts in a particular solvent can have an influence on the esterification process. The greater solubility of free-acid permits a greater reactivity than the carboxylate salt, which lacks an acid functionality. Accordingly, the yields of the corresponding esters tend to be significantly greater than the control samples when comparing the two sets of reactions. The reactions of Examples 4-7 yielded significantly greater amounts of corresponding diesters than that of Examples 1-3. The carboxylic acid itself may be sufficient to catalyze the esterification reaction under the present operational temperature and pressure conditions. One can adjust the substrate solubility for successful esterification according to the present method.

B

Example: Hydrogenation

Using a process like one of those described in the references cited above, one can perform direct hydrogenation of the carboxylic acid esters collected from the esterification process described above. For examples, one can use metallic copper catalysts for the hydrogenation of dialkyl succinate esters to BDO, GBL, and THF. The following describes an illustration of the hydrogenation process.

The copper catalysts were prepared by wet impregnation of copper salts onto the following supports (all −16+30 mesh): silica-alumina (93% silica, 7% alumina Sigma Chemicals) and two chromatographic silicas (Phase Separations, Inc.) (XOA-400 and XOB-030). Ten milliliters of solution containing copper nitrate to produce the desired loading was added to 10 g of support. The slurry was stirred at room temperature for 2 hrs. and then dried for 2 hrs. under vacuum at 60° C.-70° C. The dried solid was then calcined in air in a furnace at 500° C. for 11-12 h to give copper oxides. The catalyst material was then loaded into the reactor and reduced in-situ in pure hydrogen at 200° C. and 200 psig for 3 hrs. Catalyst supports were characterized before and after reaction by nitrogen BET surface area and mercury porosimetry. Support acidity measurements were made using n-butylamine as a titrant in dry benzene with p-dimethylaminazobenzene ($pK_a$=3.9) as the indicator.

A cone closure reactor (Autoclave Engineers, Inc.) made of 316 Stainless Steel, 167 mm long×5 mm inner diameter (i.d.), was charged with one gram of catalyst supported on a quartz frit. The reactor was surrounded by a clamshell furnace controlled by an Omega series CN-2010 programmable temperature controller. Dimethyl succinate was fed to the top of the reactor as 30 wt % solution in methanol using a Biorad HPLC pump. Hydrogen gas was also fed to the top of the reactor from a standard tank and high-pressure regulator; a rotameter was used to monitor gas flow rate at the reactor outlet. The liquid feed rate was fixed at 0.05 mL/min, and the hydrogen rate was set at 400 mL of STP/min to give a weight hourly space velocity (WHSV) of 0.9 g of DMS/g of cat/h and a $H_2$/succinate ratio of 200:1.

Condensable products were collected in single-ended 10 mL Whitey sample cylinders immersed in ice baths. Three-way valves were used to divert reaction products to either of two sample cylinders: during reaction, condensable products were collected in the traps for a timed period, after which the trap was removed and weighed and the contents were removed for analysis. Gas exiting the collection cylinders passed through a rupture disk assembly and was stepped down to atmospheric pressure using a back-pressure regulator. Gas products were collected in gas bags for analysis using gas chromatography to quantify non-condensable product formation.

Condensable products were weighed following collection and analyzed in a Varian 3300 gas chromatograph equipped with a flame ionization detector and a Supelco SPB-1 wide-bore (0.5 mm) capillary column (50-200° C. @ 12° C./min, hold @ 200° C.). Methyl lactate was used as an internal standard to facilitate the calculation of product concentrations.

Example: Hydrogenolysis

The esters resulting from the fermentation extraction described above is then hydrogenolyzed over a catalyst (e.g., reduced CuO/ZnO), which should obtain high conversions (>98%) and selectivities (e.g., International Patent Application No. WO 82/03854).

Alternatively, one can proceed according to a process such as described in U.S. Pat. No. 4,584,419. A stainless steel with an oil jacket maintained at 231° C. was used for this reaction. Hydrogen was introduced by way of a pressure regulator and flow controller (not shown) through line to the bottom end of a vaporizer containing a number of steel balls. Ester was metered as a liquid to vaporiser through a line. The resulting vaporous mixture of ester and hydrogen was passed through preheating coil to reactor. This contained a layer of glass balls, on which rested the catalyst bed. The remainder of the reactor was filled with glass balls and the upper end of the reactor was fitted with an exit tube which led to a condenser (not shown) and then to a pressure let-down valve. The exit gas flow rate was measured downstream from the condenser using a wet gas meter.

A charge of 30 ml of a granulated copper chromite catalyst was placed in the reactor which was then purged with nitrogen at 42 bar. The oil bath was raised to a temperature of 231.degree. C. A 2% $H_2$ in $N_2$ gaseous mixture at 42 bar was then passed over the catalyst for 8 hours, followed by 10% $H_2$ in $N_2$ (still at 42 bar) for a further 16 hours, and then by pure $H_2$ (also at 42 bar) for an additional 12 hours.

Diethyl succinate was then introduced into the vaporizer corresponding to a liquid hourly space velocity of 0.2/hr. The hydrogen gas:ester molar ratio in the vaporous mixture was 313:1. The temperature of the sand bath was maintained at 231° C. The condensate was analyzed by gas chromatography using a 1.82 meter long stainless steel column with an internal diameter of 3.18 mm containing 10% diethylene glycol succinate on Chromosorb PAW, a helium gas flow rate of 30 ml/minute and a flame ionisation detector. The instrument was fitted with a chart recorder having a peak integrator and was calibrated using a mixture of diethyl maleate, dialkyl succinate, butyrolactone, butane-1,4-diol, tetrahydrofuran and water of known composition. The exit gas was also sampled and analyzed by gas chromatography using the same technique. The identity of the peaks was confirmed by comparison of the retention times observed with those of authentic specimens of the materials in question and by mass spectroscopy. The following compounds were detected in the reaction mixture: diethyl succinate, butyrolactone, butane-1,4-diol, tetrahydrofuran and water. Trace amounts of minor byproducts, including 2-ethoxytetrahydrofuran and 2-ethoxybutane-1,4-diol were also detected in the reaction mixture. From the results obtained it appeared that diethyl succinate had been smoothly converted to products with a selectivity to tetrahydrofuran of 52.2 mol %, a selectivity to n-butanol of 11.6 mol %, a selectivity to gamma-butyrolactone of 26.1 mol %, and a selectivity to butane-1,4-diol of 10.1 mol %, the balance being minor byproducts.

The present invention has been described in general and in detail by way of examples. Persons of skill in the art understand that the invention is not limited necessarily to the embodiments specifically disclosed, but that modifications and variations may be made without departing from the scope of the invention as defined by the following claims or their equivalents, including other equivalent components presently known, or to be developed, which may be used within the scope of the present invention. Therefore, unless changes otherwise depart from the scope of the invention, the changes should be construed as being included herein.

The invention claimed is:

1. A process for producing a biofuel comprising: a) using a fermentation broth containing at least one free carboxylic acid; b) synthesizing an ester by reacting said free carboxylic acid with an alcohol solvent under a $CO_2$ atmosphere in substantial absence of any other acid catalyst at either a reaction temperature or pressure or both that is at a supercritical, critical or near critical condition for at least one of the alcohol or $CO_2$; and c) subjecting said ester to either hydrogenolysis or hydrogenation to form a biofuel.

2. The process according to claim 1, further comprising recovering said biofuel.

3. The process according to claim 1, wherein said biofuel is an alkane or an alcohol.

4. The process according to claim 3, wherein said biofuel includes at least one of the following: ethane, ethanol, propane, propanol, butane, 1-butanol, octane, and octanol.

5. The process according to claim 1, further comprising drying said fermentation broth into a powder before ester synthesis.

6. The process according to claim 1, further comprising concentrating said ester before either hydrogenolysis or hydrogenation.

7. The process according to claim 1, further comprising purifying said ester to at least 90% purity.

8. The process according to claim 1, wherein said fermentation broth is at a pH in a range between about 1.5 and about 4.5.

9. The process according to claim 1, wherein said alcohol solvent has an R-group of $C_1$-$C_{20}$, and is at least one of a saturated, unsaturated, cyclic, or aromatic species.

10. The process according to claim 1, wherein said carboxylic acid is selected from the group consisting of: formic acid, acetic acid, propionic acid, lactic acid, butyric acid, isobutyric acid, valeric acid, hexanoic acid, heptanoic acid, decanoic acid, lauric acid, myristic acid, and $C_{15}$-$C_{18}$ fatty acids, fumaric acid, itaconic acid, malic acid, succinic acid, maleic acid, malonic acid, glutaric acid, glucaric acid, oxalic acid, adipic acid, pimelic acid, suberic acid, azelaic acid, sebacic acid, dodecanedioic acid, glutaconic acid, ortho-phthalic acid, isophthalic acid, terephthalic acid, citric acid, isocitric acid, aconitic acid, tricarballylic acid, and trimesic acid.

11. The process according to claim 1, wherein said carboxylic acid is a polycarboxylic acid.

12. The process according to claim 11, wherein said carboxylic acid is a dicarboxylic or a tricarboxylic acid.

13. The process according to claim 11, wherein when said carboxylic acid is a polycarboxylic acid, said ester is at least a diester.

14. The process according to claim 11, wherein said polycarboxylic acid is converted to a corresponding ester at a rate of at least 50% of said polycarboxylic acid.

15. The process according to claim 1, wherein said reaction temperature is between about 150° C. and about 250° C., and said pressure is in a range between about 400 psi and 3,000 psi.

16. The process according to claim 1, wherein said free carboxylic acids are not subject to activation with a halide to form an acyl halide.

* * * * *